(12) United States Patent
Stelzig et al.

(10) Patent No.: US 9,603,780 B2
(45) Date of Patent: Mar. 28, 2017

(54) DENTAL COMPOSITION

(75) Inventors: Simon Stelzig, Constance (DE);
Joachim E. Klee, Radolfzell (DE);
Andreas Facher, Gundetswil (CH);
Christoph Weber, Constance (DE)

(73) Assignee: Dentsply International Inc.

( * ) Notice: Subject to any disclaimer, the term of this patent is extended or adjusted under 35 U.S.C. 154(b) by 628 days.

(21) Appl. No.: 13/979,811

(22) PCT Filed: Oct. 18, 2011

(86) PCT No.: PCT/EP2011/005232
§ 371 (c)(1),
(2), (4) Date: Oct. 22, 2013

(87) PCT Pub. No.: WO2012/052160
PCT Pub. Date: Apr. 26, 2012

(65) Prior Publication Data
US 2014/0039087 A1 Feb. 6, 2014

(30) Foreign Application Priority Data
Oct. 19, 2010 (EP) .................................... 10013771

(51) Int. Cl.
| | | |
|---|---|---|
| B29C 47/92 | (2006.01) |
| A61K 6/083 | (2006.01) |
| A61K 6/00 | (2006.01) |
| A61K 6/02 | (2006.01) |
| C07C 233/31 | (2006.01) |
| C08F 290/06 | (2006.01) |
| C07C 233/20 | (2006.01) |

(52) U.S. Cl.
CPC ............ A61K 6/083 (2013.01); A61K 6/0023 (2013.01); A61K 6/0835 (2013.01); C07C 233/20 (2013.01)

(58) Field of Classification Search
None
See application file for complete search history.

(56) References Cited

U.S. PATENT DOCUMENTS

| | | | |
|---|---|---|---|
| 3,655,605 A | 4/1972 | Smith et al. |
| 3,814,717 A | 6/1974 | Wilson et al. |
| 4,016,124 A | 4/1977 | Crisp et al. |
| 4,035,321 A | 7/1977 | Shahidi et al. |
| 4,089,830 A | 5/1978 | Tezuka et al. |
| 4,143,018 A | 3/1979 | Crisp et al. |
| 4,209,434 A | 6/1980 | Wilson et al. |
| 4,317,681 A | 3/1982 | Beede et al. |
| 4,342,677 A | 8/1982 | Muramatsu et al. |

(Continued)

FOREIGN PATENT DOCUMENTS

| | | |
|---|---|---|
| DE | 19607641 A1 | 9/1997 |
| DE | 10058829 A1 | 6/2002 |

(Continued)

*Primary Examiner* — Peter A Salamon
(74) *Attorney, Agent, or Firm* — Douglas J Hura; Leana Levin; David A. Zdurne

(57) ABSTRACT

Dental composition comprising a water-soluble polymerizable compound of the following formula (1): wherein A is a linear or branched linker group represented by the following formula (3), wherein the nitrogen atom of at least two of the termini forms an amide bond with an X moiety; wherein R' represents a hydrogen atom or a substituted or unsubstituted aliphatic or cycloaliphatic hydrocarbon group, wherein each R may be the same or different $L^1$, $L^2$, and $L^3$ which may be the same or different, independently represent a single bond, or a $C_{2-20}$ straight-chain, branched or cyclic hydrocarbon group optionally containing from 1 to 6 heteroatoms selected from nitrogen and oxygen in the backbone of the hydrocarbon group, and optionally from 1 to 6 functional groups selected from carboxylic acid groups or a salt thereof, hydroxyl groups, thiol groups and amino groups, and in case a plurality of $L^1$ and $L^2$ are present, each of $L^1$ and $L^2$ may be the same or different; $Q_1$ and $Q_2$, which may be the same or different, independently represent a single bond or a linkage selected from an amide, a urethane, a urea and a thiourea linkage; k is an integer of at least 0, X are moieties containing a polymerizable double bond and forming an amide bond with a nitrogen atom of A, wherein each X may be the same or different and are represented by the following formula (2): wherein $R^1$ and $R^2$ are independent from each other and represent a hydrogen atom, a $C_{1-6}$ alkyl group or a group —$(CH_2)_m$—COOM, wherein M represents a hydrogen atom or a metal atom, m is an integer of from 0 to 6, L is a bond or a $C_{1-6}$ alkylene group; and n is an integer of at least 2; (ii) an initiator system; optionally a polyacidic polymer; optionally water and/or a water soluble solvent; and optionally a particulate filler.

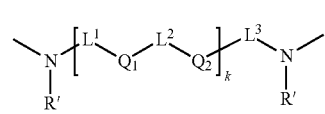

(3)

13 Claims, No Drawings

(56) References Cited

U.S. PATENT DOCUMENTS

| | | | |
|---|---|---|---|
| 4,360,605 A | 11/1982 | Schmitt et al. | |
| 4,374,936 A | 2/1983 | Tomioka et al. | |
| 4,376,835 A | 3/1983 | Schmitt et al. | |
| 4,518,749 A * | 5/1985 | Waddill | C08G 59/423 525/504 |
| 5,130,347 A | 7/1992 | Mitra | |
| 5,154,762 A | 10/1992 | Mitra et al. | |
| 6,953,832 B2 | 10/2005 | Moszner et al. | |
| 2003/0232944 A1 | 12/2003 | Molenberg et al. | |
| 2004/0266906 A1 * | 12/2004 | Klee | A61K 6/0023 523/118 |
| 2007/0293642 A1 * | 12/2007 | Klee | A61K 6/0023 526/193 |
| 2014/0039087 A1 * | 2/2014 | Stelzig | A61K 6/0023 523/113 |

FOREIGN PATENT DOCUMENTS

| | | | |
|---|---|---|---|
| DE | 10058830 A1 | 6/2002 | |
| DE | WO 03035013 A1 * | 5/2003 | A61K 6/0023 |
| EP | 0797972 A2 | 10/1997 | |
| EP | 2058318 A1 | 5/2009 | |
| JP | 2005065902 A | 3/2005 | |
| JP | 2006512466 A | 4/2006 | |
| WO | 92/21632 A2 | 12/1992 | |
| WO | 95/27008 A1 | 10/1995 | |
| WO | 00/05182 A1 | 2/2000 | |
| WO | 02/41845 A1 | 5/2002 | |
| WO | 02/092021 A1 | 11/2002 | |
| WO | 03/013444 A1 | 2/2003 | |
| WO | 03/035013 A1 | 5/2003 | |
| WO | 2008121895 A1 | 10/2008 | |

* cited by examiner

DENTAL COMPOSITION

FIELD OF THE INVENTION

The present invention relates to a dental composition containing a specific hydrolysis-stable water-soluble compound. Moreover, the present invention relates to the use of the specific hydrolysis-stable compound for the preparation of a dental composition, in particular a dental adhesive or dental restorative composition. The specific hydrolysis-stable water-soluble compound of the present invention is resistant to an acidic medium so that the dental composition of the present invention may be formulated as an acidic one-component composition, or as a dental cement.

BACKGROUND OF THE INVENTION

Hard dental tissue having suffered damage due to dental caries is conventionally restored by a procedure in which an indirect restoration such as a crown, a bridge, an inlay, or an onlay, is adhered on the damaged portion of the hard dental tissue with a specific dental composition such as a dental resin cement. Alternatively, damaged hard dental tissue may be restored by using a direct restorative material which is applied as an uncured dental composition such as a dental composite, and hardened.

A dental resin cement and a dental composite are required to have low shrinkage, sufficient adhesion and high material strength. Otherwise, not only the dental composition may be released from the hard dental tissue after some time under the severe conditions of the oral environment, but also a gap may be produced at an interface between the dental composition and the teeth, and bacteria may invade onto the exposed surfaces and impose an adverse effect on dental pulp. Given that the use of a dental primer increases the complexity of a dental procedure, a simple adhesion procedure is desired which uses a dental composition which does not require a primer treatment for such various adherents.

Moreover, since adhesion of a dental composition to hard dental tissue requires the presence of acidic groups in the composition, the dental composition desirably has a high hydrolysis stability in order to avoid degradation of the composition during storage or when applied to hard dental tissue.

Japanese Patent Publication No. 2006-512466A discloses a resin cement which does not require a primer. The polymerizable composite material comprises at least one multifunctional monomer containing an acid in a concentration range of about 10-85% by weight, a non-reactive filler in a concentration range of about 1-80% by weight, a polymerization system in a concentration range of about 1.5-25% by weight, and water in a concentration range of about 0.1-25% by weight. However, since such the composition uses a single acidic monomer, sufficient adherability cannot be attained for both of enamel and dentin.

International Publication No. WO 02/092021A1 discloses a dental resin cement composition consisting of a liquid and a powder. A powder-liquid type resin cement, is inferior in handling properties upon mixing as compared with a paste-and-paste type resin cement.

Japanese Patent Publication No. 2005-65902A discloses a dental adhesive composition comprising, as an essential adhesive component, a carboxylic acid compound having one (meth)acryloyl group and one carboxyl group which are bound to an aromatic group as a polymerizable monomer containing a particular carboxylic acid group. However, such the polymerizable monomer having an ester group quickly degrades in an acidic medium.

Dental materials based on polyfunctional amides are known from U.S. Pat. No. 6,953,832 which contain specific polymerizable amides and optionally strongly acidic polymerizable monomers such as dipentaerythritol pentamethacryloyloxy dihydrogenphosphate. Filler containing compositions are suggested. However, U.S. Pat. No. 6,953,832 does not disclose a composite.

SUMMARY OF THE INVENTION

It is an object of the present invention to provide dental compositions, in particular dental cements, which are useful as filling materials, cavity liners and bases, cements, pit and fissure sealants to prevent caries, as adhesive between tooth structure and/or bone and polymeric composites, whereby the dental composition has excellent storage stability and long term mechanical resistance, and whereby the composition may be applied directly on the dental surface.

A further object is to provide dental restorative/prosthetic compositions that are relatively inexpensive and easy to manufacture.

The present invention provides a dental composition comprising (i) a water-soluble polymerizable compound having one or more acidic groups, of the following formula (1):

$$AX_n \quad (1)$$

wherein

A is a linear or branched linker group represented by the following formula (3), wherein the nitrogen atom of at least two of the termini forms an amide bond with an X moiety;

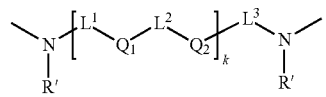

wherein

R' represents a hydrogen atom or a substituted or unsubstituted aliphatic or cycloaliphatic hydrocarbon group, wherein each R' may be the same or different;

$L^1$, $L^2$, and $L^3$ which may be the same or different, independently represent a single bond, or a $C_{2-20}$ straight-chain, branched or cyclic hydrocarbon group optionally containing from 1 to 6 heteroatoms selected from nitrogen and oxygen in the backbone of the hydrocarbon group, and optionally from 1 to 6 functional groups selected from carboxylic acid groups or a salt thereof, hydroxyl groups, thiol groups and amino groups, and in case a plurality of $L^1$ and $L^2$ are present, each of $L^1$ and $L^2$ may be the same or different;

$Q_1$ and $Q_2$, which may be the same or different, independently represent a single bond or a linkage selected from an amide, a urethane, a urea and a thiourea linkage;

k is an integer of at least 0,

X are moieties containing a polymerizable double bond and forming an amide bond with a nitrogen atom of A, wherein each X may be the same or different and are represented by the following formula (2):

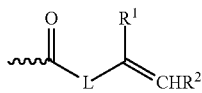
(2)

wherein
$R^1$ and $R^2$ are independent from each other and represent a hydrogen atom, a $C_{1-6}$ alkyl group or a group $—(CH_2)_m—COOM$, wherein M represents a hydrogen atom or a metal atom, m is an integer of from 0 to 6,
L is a bond or a $C_1$ alkylene group; and
n is an integer of at least 2;
(ii) an initiator system;
(iii) optionally a polyacidic polymer which may have polymerizable double bonds;
(iv) optionally water and/or a water soluble solvent; and
(v) optionally a particulate filler.

Moreover, the present invention relates to a compound of formula (1) as defined above.

Moreover, the present invention provides a use of the compound of formula (1) as defined above, in particular for the preparation of a dental composition.

Moreover, the present invention provides a process for preparing a compound of formula (1), which comprises
(i) a step of a step-growth polymerization of a mixture containing a polyamine and a compound having at least two carboxylic acid groups or an anhydride thereof, optionally in the presence of a compound of the following formula (5a) for obtaining a polyamide:

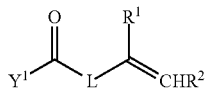
(5a)

wherein L, $R^1$ and $R^2$ are as defined in claim 1, and $Y^1$ is a leaving group or $Y^1$ forms an intramolecular anhydride group together with a carboxyl group present in $R^1$ or $R^2$ and the adjacent carbonyl group; and
(ii) a step of introducing moieties of the formula (2) by reacting the polyamide obtained in step (i) with a compound of formula (5a) wherein $Y^1$ is a leaving group and $R^1$ and $R^2$ are as defined above; or
(iii) a step of reacting a mixture containing a polyamine and a compound of formula (5a) for obtaining an amide: and
(iv) a step of a step-growth polymerization of a mixture containing the amide obtained in (iii) and a compound having at least two carboxylic acid groups, or an anhydride thereof for obtaining the water-soluble polymerizable compound of the formula (1).

The dental compositions according to the invention contain a mixture of hydrolysis-stable polymerizable components including a compound of formula (1). Preferably, the mixture contains at least a crosslinking polymerizable monomer and an acidic polymerizable monomer. The polymerizable monomers are hydrolysis-stable. Specifically, the polymerizable monomers do not contain groups such as ester groups, in the main chain which hydrolyze in aqueous media at pH 3 at room temperature within one month.

DESCRIPTION OF THE PREFERRED EMBODIMENTS

The dental composition of the present invention comprises a water-soluble polymerizable compound having one or more acidic groups, of the following formula (1):

$$AX_n \quad (1)$$

The polymerizable compounds of formula (1) comprise a moiety A, and at least one substituent X. The polymerizable compounds of formula (1) has one or more acidic groups, namely carboxylic acid groups or a salt thereof. Moreover, A is a linker group containing least n nitrogen atoms. The linker has a valency of at least two which corresponds to the total number of substituents X. Accordingly, A may be preferably divalent (n=2), trivalent (n=3), tetravalent (n=4), pentavalent (n=5), or hexavalent (n=6). Preferable A is divalent or trivalent, most preferably divalent.

Preferably, the linker group may be a linear or branched monomeric, oligomeric, polymeric or copolymeric group containing nitrogen atoms at the terminal positions for forming an amide bond with a moiety X. A monomeric groups is a low-molecular group having a molecular weight of up to 500. An oligomeric group is a group having a molecular weight of more than 500 to up to 10000 and may be prepared by a polymerization reaction. A polymeric or copolymeric group is a group having a molecular weight of more than 10000 which may be obtained by a polymerization reaction. The polymerization may be a condensation or addition polymerization.

The linker group is a linear or branched group represented by the following formula (3), wherein the nitrogen atom of at least two of the termini forms an amide bond with an X moiety:

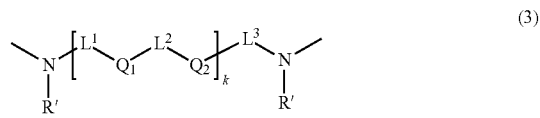
(3)

In formula (3), R' represents a hydrogen atom or a substituted or unsubstituted aliphatic or cycloaliphatic hydrocarbon group. Substituents of the aliphatic or cycloaliphatic hydrocarbon group may be selected from hydroxyl groups, thiol groups, amino groups, or carboxylic acid groups or a salt thereof. The R' may be the same or different. According to a preferred embodiment, R' is a hydrogen atom. According to a further preferred embodiment, R' is a lower alkyl group having 1 to 6 carbon atoms, more preferably, 1 to 3 carbon atoms.

In formula (3), $L^1$, $L^2$, and $L^3$ may be the same or different. In case a plurality of $L^1$ an $L^2$ are present when k is at least 2, each of $L^1$ and $L^2$ may be the same or different. Preferably, each of $L^1$ and each of the plurality $L^2$ are the same.

$L^1$, $L^2$, and $L^3$ independently represent a single bond, or a $C_{2-20}$ straight-chain, branched or cyclic hydrocarbon group containing from 1 to 6 heteroatoms selected from nitrogen and oxygen in the backbone of the hydrocarbon group, and optionally from 1 to 6 functional groups selected from carboxylic acid groups or a salt thereof, hydroxyl groups, thiol groups and amino groups. In a particular embodiment, $L^1$, $L^2$, and $L^3$ do not carry an optional functional group. Preferably, at least one, more preferably at least two of $L^1$, $L^2$, and $L^3$, do not represent a single bond. Preferably, $L^1$, $L^2$, and $L^3$ contain 1 or 2 heteroatoms selected from nitrogen, and oxygen in the backbone of the hydrocarbon group. Preferably, the hydrocarbon group has 1 to 6 carbon atoms and contains 1 or 2 heteroatoms selected from nitrogen, and oxygen in the backbone of the hydrocarbon group, and optionally from 1 to 3 carboxylic acid groups or a salt thereof.

In formula (3), $Q_1$ and $Q_2$, may be the same or different. $Q_1$ and $Q_2$ may represent a single bond or a linkage selected from an amide, a urethane, a urea and a thiourea linkage. Preferably, at least one of $Q_1$ and $Q_2$ is not a single bond. In case $Q_1$ and $Q_2$ represent an amide or urethane linkage, the orientation of the amide or urethane linkage may be the same or different.

In formula (3), k is an integer of at least 0. When k is 0, then $L^3$ preferably is not a single bond. Preferably, k is in the range of from 0 to 500, more preferably from 1 to 40.

According to a further preferred embodiment, the polymerizable compound of formula (1) contains one or more acidic groups selected from carboxylic acid groups, phosphonic acid groups, sulfonic acid groups or phosphoric acid ester groups.

In formula (1), X are moieties containing a polymerizable double bond and forming an amide bond with a nitrogen atom of A, which X may be the same or different and are represented by the following formula (2).

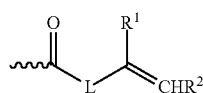
(2)

In formula (2), $R^1$ and $R^2$ are independent from each other and represent a hydrogen atom, a $C_{1-6}$ alkyl group or a group —$(CH_2)_m$—COOM, wherein M is a hydrogen atom or a metal atom and m is an integer of from 0 to 6. The metal atom may be an alkali metal atom or an alkaline earth metal. In case of an alkaline earth metal, the second charge on the metal atom is neutralized by either a further carboxylic acid anion or another anion. Preferably, $R^1$ is single bond or a methyl group. Preferably, $R^2$ is a hydrogen atom or a group —$(CH_2)_m$—COOH, wherein m is 0, 1 or 2.

In formula (2), L is a bond or a $C_{1-6}$ alkylene group, preferably a single bond or a methylene or ethylene group.

The linker group imparts water solubility to the compound of formula (1). Water solubility within the sense of the present invention means that the compound of formula (1) can be dissolved as a 0.1 percent by weight solution in water at 25° C. Preferably, the compound of formula (1) of the present invention has a water solubility of at least 2.0 weight % in water at 25° C.

Preferably, the linker group is a polyamide group obtainable by a process comprising the step of a step-growth polymerization including a condensation reaction or addition reaction of a mixture containing a polyamine having a moiety of the formula (3) and additional hydrogen atoms, and a compound of the following formula (4) having at least two carboxylic acid groups, said carboxylic acid groups may be present in the form of an anhydride:

MOOC—$R^5$—COOM (4)

optionally in the presence of a compound of the following formula (5a):

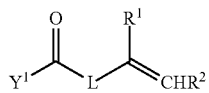
(5a)

wherein $R^5$, L, $R^1$ and $R^2$ are as defined in above, M is a hydrogen atom or a metal atom which is preferably monovalent, and $Y^1$ is a leaving group or $Y^1$ forms an intramolecular anhydride group together with a carboxyl group present in $R^1$ or $R^2$ and the adjacent carbonyl group. The monovalent metal atom is preferably an alkali metal.

Preferably, the compound of formula (5a) is itaconic acid or a lactone or a carboxylic anhydride thereof.

The reaction conditions are not particularly limited. According to a preferred embodiment, a polyamine having a moiety of the formula (3) and additional hydrogen atoms is dissolved in a suitable aprotic solvent such as dimethylsulfoxide. Moreover, a compound of formula (4) is separately dissolved in a suitable aprotic solvent such as dimethylsulfoxide. Both solutions are then simultaneously added dropwise at ambient temperature into a round bottom flask. It is preferable to add a suitable stabilizer such as BHT. The reaction mixture is stirred. The reaction time may be from 1 hour to 30 hours. The reaction temperature is preferably in the range of from −10° C. to the boiling point of the solvent. Preferably, the reaction is carried out at ambient temperature. The product may be precipitated twice from from a suitable solvent wherein the product is insoluble. As an examples of such a solvent diethylether may be mentioned.

The process for the preparation of the polymerizable compound of the formula (1) according to the present invention comprises (i) a step of a step-growth polymerization of a mixture containing a polyamine and a compound having at least two carboxylic acid groups or an anhydride thereof, optionally in the presence of a compound of the following formula (5a) for obtaining a polyamide:

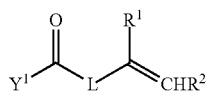
(5a)

wherein L, $R^1$ and $R^2$ are as defined in claim 1, and $Y^1$ is a leaving group or $Y^1$ forms an intramolecular anhydride group together with a carboxyl group present in $R^1$ or $R^2$ and the adjacent carbonyl group.

The process further may further comprise a step of introducing the moieties of the formula (2) by reacting the polyamide obtained in step (i) with a compound of formula (5a) wherein $Y^1$ is a leaving group and $R^1$ and $R^2$ are as defined above; or a step of reacting a mixture containing a polyamine and a compound of formula (5a) for obtaining an amide.

The process may also comprise a step of a step-growth polymerization of a mixture containing the amide obtained in (iii) and a compound having at least two carboxylic acid groups or an anhydride thereof for obtaining the water-soluble polymerizable compound of the formula (1).

Preferably, the water soluble polymerizable compound of formula (1) has an average molecular weight of from 300 to 100,000, more preferably 400 to 10,000 Da.

The dental composition according to the present invention comprises an initiator system. The initiator system may be based on a redox initiator or on a photoinitiator.

In case the dental composition contains a redox initiator, the amount of reducing agent and oxidizing agent should be sufficient to provide the desired degree of polymerization. Preferably, the mixed but unset cements of the invention contain a combined weight of about 0.01 to about 10%, more preferably about 0.2 to about 5%, and most preferably about 0.3 to about 3% of the reducing agent and oxidizing agent, based on the total weight (including water) of the mixed but unset cement components. The reducing agent or the oxidizing agent can be microencapsulated as described in U.S. Pat. No. 5,154,762. This will generally enhance shelf stability of the cement parts and if necessary permit packaging both the reducing agent and oxidizing agent together. Water-soluble and water-insoluble encapsulants can be employed. Suitable encapsulating materials include cellulosic materials as cellulose acetate, cellulose acetate butyrate, ethyl cellulose, hydroxymethyl cellulose and hydroxyethyl cellulose being preferred. Other encapsulants include polystyrene, copolymers of polystyrene with other vinylic monomers and polymethylmethacrylate, copolymers of methylmethacrylate with other ethylenically-unsaturated monomers. Preferred encapsulants are ethylcellulose and cellulose acetate butyrate. By varying the choice of encapsulant and the encapsulation conditions, the onset of curing can be tailored to start at times ranging from seconds to minutes. The ratio of amount of encapsulant to activator generally ranges from 0.5 to about 10 and preferably from about 2 to about 6.

Suitable oxidizing agents (initiators) include peroxides such as benzoyl peroxide, cumene hydroperoxide (CHP) and tert-butyl hydroperoxide, ferric chloride, hydroxylamine (depending upon the choice of reducing agent), perboric acid and its salts, and salts of a permanganate or persulfate anion. Preferred oxidizing agents are peroxides, potassium persulfate, ammonium persulfate and hydrogen peroxide.

Suitable reducing agents (activators) include ascorbic acid, benzyl thiourea, ferrous chloride, ferrous sulfate, hydrazine, hydroxylamine (depending upon the choice of oxidizing agent) oxalic acid, thiourea, and salts of a dithionite or sulfite anion. Preferred reducing agents include ascorbic acid and ferrous sulfate.

A photoinitiator should be capable of promoting polymerization of the polymerizable groups on exposure to light of a suitable wavelength and intensity. The photoinitiator preferably is sufficiently shelf-stable and free of undesirable coloration to permit its storage and use under typical dental conditions. Visible light photoinitiators are preferred. Suitable visible light-induced and ultraviolet light-induced initiators include an alpha-diketone (e.g., camphorquinone) with or without additional hydrogen donors (such as sodium benzene sulfinate, amines and amine alcohols). The photoinitiator may be present in an amount sufficient to provide the desired rate of photopolymerization. This amount will be dependent in part on the light source, the thickness of the cement layer to be exposed to radiant energy and the extinction coefficient of the photoinitiator. Preferably, mixed but unset photocurable cements of the invention will contain about 0.01 to about 5%, more preferably from about 0.1 to about 2% photoinitiator, based on the total weight (including water) of the mixed but unset cement components.

The dental composition according to the present invention may contain further polymeric components, such as a polymer having acidic groups.

To effect cross-linking or additional cross-linking of the dental composition, one or more comonomers may be included in the dental composition. Suitable comonomers contain at least one polymerizable functional group. Suitable polymerizable functional groups are ethylenically unsaturated groups (e.g. alkenyl groups and preferably vinyl groups). Ethylenically unsaturated groups are polymerisable by a free radical mechanism. Preferred examples are substituted and unsubstituted acrylates, methacrylates, or alkenes.

A dental composition is prepared by mixing the components of the dental composition of the present invention. The components of the dental composition can be combined (such as by mixing or blending) in a variety of manners and amounts in order to form the dental composition of the present invention.

For example, in a dental cement, a concentrated solution of the polymerizable compound, and the initiator system may be mixed with the particulate filler and optionally further components such as an ionomer, at the time of use.

Alternatively, the polymerizable compound, the initiator system, the particulate filler and optionally an ionomer are provided as a freeze-dried or lyophilized powdered blend under conditions in which there is not sufficient water to allow the setting reaction to proceed. Such systems can then be combined with water at the time of use in order to begin the setting reaction. Once the setting reaction has begun, the resultant mixture may be formed into its desired shape, followed by curing and allowing the mixture to fully harden.

The amount of the water-soluble polymerizable compound of formula (1) in a dental composition may be in the range of from 1 to 70% by weight based on the total weight of the composition. Preferably, the amount is in the range of from 3 to 50% by weight based on the total weight of the composition.

The reaction mixture may also include a modifying agent such as tartaric acid, for adjusting the working time and a setting time, respectively, when preparing the cement as described in U.S. Pat. No. 4,089,830, U.S. Pat. No. 4,209,434, U.S. Pat. No. 4,317,681 and U.S. Pat. No. 4,374,936. In general, an increase in working time results in an increase in setting time as well.

The "working time" is the time between the beginning of the setting reaction when the ionomer and modified particulate reactive filler are combined in the presence of water, and the time the setting reaction proceeds to the point when it is no longer practical to perform further physical work upon the system, e.g. spatulate it or reshape it, for its intended dental or medical application.

The "setting time" is the time measured from the beginning of the setting reaction in a restoration to the time sufficient hardening has occurred to allow subsequent clinical or surgical procedures to be performed on the surface of the restoration.

In a setting reaction, due to the presence of polymerizable double bonds, a polymerization reaction takes place.

A dental composition according to the present invention may further contain a polyacidic polymer, for example as a ionomer component in a dental cement. The polyacidic polymer may have polymerizable double bonds so that the polyacidic polymer may be crosslinked with the water-soluble polymerizable compound of formula (1).

Polymerizable acids used for preparing polymers useful for glass-ionomer cement systems include alkenoic acids and unsaturated mono-, di- and tricarboxylic acids. Representative alkenoic acids are described, for example, in U.S. Pat. No. 4,016,124, U.S. Pat. No. 4,089,830, U.S. Pat. No. 3,655,605; U.S. Pat. No. 4,143,018; U.S. Pat. No. 4,342,677, U.S. Pat. No. 4,360,605, U.S. Pat. No. 4,376,835 and U.S.

Pat. No. 5,130,347. Specific examples are acrylic acid, methacrylic acid, maleic acid, fumaric acid, itaconic acid, crotonic acid, and derivatives thereof, such as the acid chlorides thereof, the acid anhydrides thereof and chloro or bromo derivatives thereof. Particularly preferred monomers are acrylic acid, itaconic acid and maleic acid, and the chlorides or anhydrides thereof. The pendent carboxylic acid groups of the ionomer must be sufficient in number or percent by weight to bring about the setting or curing reaction in the presence of the modified particulate reactive and/or non-reactive filler.

Polymerizable double bonds as a source of additional covalent crosslinking, which imparts additional strength to the ultimate dental composition, may be introduced by reacting a portion of the carboxylic acid groups with a bi-functional monomer. Examples of suitable bi-functional monomers include bisacrylamides such as N,N'-diethyl-1,3-bisacrylamido-propan (BADEP), 1,3-bisacrylamido-propan (BAP), and 1,3-bisacrylamido-2-ethyl-propan (BAPEN); acryloyl chloride, methacryloyl chloride, vinyl azalactone, allyl isocyanate, 2-hydroxyethylmethacrylate (HEMA), 2-aminoethylmethacrylate, 2-isocyanatoethyl methacrylate (IEM), acrylic acid, methacrylic acid and N-vinylpyrrolidone. Other examples of suitable bi-functional monomers are described in U.S. Pat. No. 4,035,321 U.S. Pat. No. 5,130,347.

In general, the weight-to-weight ratio of an ionomer to water in a dental cement is from about 1:10 to about 10:1. In general, the concentration of ionomer in water ranges from 25 to 75% by weight, and preferably from 40 to 65 percent. The resultant aqueous solution has a weight ratio of polymer to liquid (polymer:liquid) generally ranging from about 1.5 to 8.

The dental composition may optionally comprise water and/or a water soluble solvent. Suitable solvents are nonreactive diluents such as alcohols. As examples of suitable alcohols, ethanol and propanol may be mentioned.

The amount of water and/or a water soluble solvent in the dental composition of the present invention is preferably in the range of from 5 to 90% by weight, more preferably 10 to 70 percent by weight based on the total weight of the composition.

The dental composition may optionally contain a particulate filler. In a specific embodiment, the particulate filler is reactive with a polyacid in a cement reaction. A "particulate filler" is a powdered metal oxide or hydroxide, mineral silicate, or ion leachable glass or ceramic.

Examples of reactive particulate filler materials include materials commonly known in the art of dental compositions such as calcium or strontium-containing and aluminum-containing materials. Preferably, particulate reactive fillers contain leachable fluoride ions. Specific examples of particulate reactive fillers are selected from calcium alumino silicate glass, calcium alumino fluorosilicate glass, calcium aluminumfluoroborosilicate glass, strontium aluminosilicate glass, strontium aluminofluorosilicate glass, strontium aluminofluoroborosilicate glass. Suitable particulate reactive fillers further include metal oxides such as zinc oxide and magnesium oxide, and ion-leachable glasses, e.g., as described in U.S. Pat. No. 3,655,605, U.S. Pat. No. 3,814,717, U.S. Pat. No. 4,143,018, U.S. Pat. No. 4,209,434, U.S. Pat. No. 4,360,605 and U.S. Pat. No. 4,376,835.

Suitable non-reactive fillers may be selected from fillers currently used in dental restorative compositions.

The filler may have a unimodal or polymodal (e.g., bimodal) particle size distribution. The filler can be an inorganic material. It can also be a crosslinked organic material that is insoluble in the polymerizable resin, and is optionally filled with inorganic filler. The filler can be radiopaque, radiolucent or non-radiopaque. Examples of suitable non-reactive inorganic fillers are naturally-occurring or synthetic materials such as quartz, nitrides such as silicon nitride, glasses derived from, for example Ce, Sb, Sn, Zr, Sr, Ba and Al, colloidal silica, feldspar, borosilicate glass, kaolin, talc, titania, and zinc glass, and submicron silica particles such as pyrogenic silicas. Examples of suitable non-reactive organic filler particles include filled or unfilled pulverized polycarbonates or polyepoxides. Preferably the surface of the filler particles is treated with a coupling agent in order to enhance the bond between the filler and the matrix. The use of suitable coupling agents include gamma-methacryloxypropyltrimethoxysilane, gamma-mercaptopropyltriethoxysilane, gamma-aminopropyltrimethoxysilane, and the like.

The particulate filler usually has an average particle size of from 0.005 to 100 µm, preferably of from 0.01 to 40 µm as measured using, for example, by electron microscopy or by using a conventional laser diffraction particle sizing method as embodied by a MALVERN Mastersizer S or MALVERN Mastersizer 2000 apparatus. The particulate filler may be a multimodal particulate reactive filler representing a mixture of two or more particulate fractions having different average particle sizes. The particulate reactive filler may also be a mixture of particles of different chemical composition. In particular, it is possible to use a mixture of a particulate reactive material and a particulate non-reactive material. The particulate reactive filler may be surface modified by a surface modifying agent.

The dental compositions of the present invention may further contain pigments, free radical scavengers, polymerization inhibitors, reactive diluents, surfactants (such as to enhance solubility of an inhibitor e.g. polyoxyethylene), coupling agents to enhance reactivity of fillers e.g., 3-(trimethoxysilyl) propyl methacrylate, and rheology modifiers.

An example of a suitable free radical scavenger is 4-methoxyphenol. An example of a suitable inhibitor is hydroxytoluene or butylated hydroxytoluene (BHT). The amount of inhibitor may be selected from 0.001 to 2% and preferably from 0.02 to 0.5% based on the total weight of the copolymer/comonomer/water mixture.

Suitable reactive diluents are alpha,beta unsaturated monomers for providing altered properties such as toughness, adhesion, and set time. Suitable alpha,beta-unsaturated monomers may be acrylates and methacrylates such as methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bisphenol A ("bis-GMA"), glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxyethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethyl-hexamethylene dicarbamate, di-1-methyl-2-methacryloxy-ethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxy-ethyl-trimethyl-hexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl-4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, and 2,2'-bis[3(4-phenoxy)-2-hydroxypropane-1-acryalte]propane, may be mentioned. Other suitable examples of polymerizable components are isopropenyl oxazoline, vinyl azalactone, vinyl pyrrolidone, styrene, divinylbenzene, urethane acrylates or methacrylates, epoxy acrylates or methacrylates and polyol acrylates or methacrylates. Mixtures of alpha,beta-unsaturated monomers can be added if desired. Preferably, the mixed but unset dental compositions of the invention will contain a combined weight of about 0.5 to about 40%, more preferably about 1 to about 30%, and most preferably about 5 to 20% water, solvents, diluents and alpha,beta-unsaturated monomers, based on the total weight (including such water, solvents, diluents and alpha,beta-unsaturated monomers) of the mixed but unset dental composition components.

Depending upon the application of the dental composition and the manner in which polymerization is achieved, various components of the cement may be packaged differently. For example, in the case of a redox-based system, ingredients of the dental composition composition are divided into two separate packages—the first package containing the copolymer, comonomer, the initiator and water, and the second package containing the reactive filler and the activator. In another embodiment, the first package contains all solid materials (e.g., copolymer, comonomer, reactive filler and if desired, the reducing agent, and the second package contains water and if desired, the initiator. In the case of photo-initiation, the photo-initiator can be included in either the solid (e.g. paste) or liquid parts of the dental composition.

Preferably, the dental composition of the present invention is packaged as a one-pack composition wherein all components are combined in a single composition.

A compound of formula (1) according to the present invention may be used for the preparation of a dental composition. Specifically, the dental composition may comprise the polymerizable compound of the formula (1), an initiator system, and optionally a particulate filler. The dental composition may be a dental adhesive composition or a dental restorative composition.

The invention will now be further illustrated by the following Examples. All percentages refer to percentages by weight unless stated otherwise.

EXAMPLES

Example 1

Synthesis of Amide Based Macromonomers

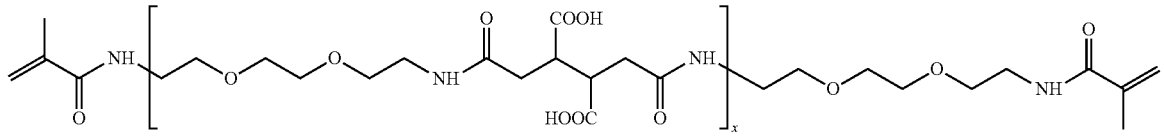

0.0025 mol (371 mg) of 2,2' ethylendioxybisethyl amine (CAS: 929-59-9) are dissolved in 5 mL DMSO. 0.0025 mol (495 mg) butane tetracarboxylic acid dianhydride are dissolved in 5 mL DMSO and 0.0006 mol (92 mg) methacrylic anhydride (CAS: 760-93-0) are added. Both solutions are simultaneously added dropwise at ambient temperature into a round bottom flask. BHT is added as a stabilizer. The reaction mixture is stirred for 16 h at ambient temperature. Das product is precipitated twice from diethyl ether, redissolved in the least amount of ethanol and extracted again with diethyl ether.

Calculated degree of polymerization (end group analysis by NMR): x about 8.

IR: $\nu$ (in $cm^{-1}$)=3294, 3083, 2949-2873, 1719, 1649, 1543

1H-NMR (DMSO-$d_6$, 400 MHz)=12,280 (s, COOH), 8,005-7,570 (m, CONH), 5.636+5.311 (s, $CH_2CCH_3COO$, vinylic protons), 3,476-3,154 (m), 1,832 (s, $CH_2CCH_3COO$) ppm.

Example 2

Variation of Concentration of Methacrylic Anhydride

The reaction was conducted as described above, with the exception of the addition of 0.0013 mol (200 mg) methacrylic anhydride.

Calculated degree of polymerisation (end group analysis by NMR): x about 6.

Example 3

Variation of Concentration of Methacrylic Anhydride

The reaction was conducted as described above, with the exception of the addition of 0.0003 mol (46 mg) methacrylic anhydride.

Calculated degree of polymerisation (end group analysis by NMR): x about 15.

The products obtained according to Examples 1 to 3 are water soluble: 100 mg of the respective product may be dissolved in 100 mg $H_2O$. Upon addition of 5 mg of VA-044 as a polymerization initiator to the solutions and heating at 50° C., a gel is formed within a few minutes.

Example 4

Macromonomer 1

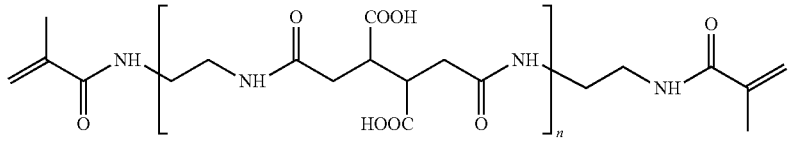

0.088 mol (5.34 g) of ethylenediamine (CAS: 107-15-3) were dissolved in 16 mL DMSO. 0.040 mol (7.93 g) butane tetracarboxylic dianhydride were dissolved in 72 mL DMSO and 0.088 mol (14.43 g) methacrylic acid anhydride (CAS: 760-93-0) were added thereto. Both solutions were simultaneously added dropwise to a flask over the same period of time. BHT was added to the mixture as a stabilizer. The reaction mixture is stirred for 16 hours at room temperature. The product may subsequently be precipitated with a suitable solvent (ethyl acetate, diethyl ether oder tert.-butylmethyl ether). The resulting precipitate is isolated and dried.

Calculated degree of polymerisation (end group analysis, NMR): x≈2.

IR: ν(in $cm^{-1}$)=3290, 3079, 2920, 1716, 1650, 1534

$^1$H-NMR (DMSO-$d_6$, 400 MHz)=8,149-7,806 (m, CONH), 5.683+5.332 (ps, $CH_2CCH_3COO$, vinylic protonen), 3.130-2.769 (m, backbone), 2.504-2.106 (m, backbone), 1.831 (s, $CH_2CCH_3COO$) ppm.

The product obtained is soluble in wate at a weight ration of product:wate of 1:1.

Example 5

Macromonomer 2

0.044 mol (2.64 g) ethylenediamine (CAS: 107-15-3) are dissolved in 16 mL DMSO. 0.040 mol (7.93 g) butane tetracarboxyalic acid dianhydride are dissolved in 72 mL DMSO and 0.044 mol (6.78 g) methacrylic acid anhydride (CAS: 760-93-0) is added thereto. Both solutions were simultaneously added dropwise to a flask over the same period of time. BHT was added to the mixture as a stabilizer. The reaction mixture is stirred for 16 hours at room temperature. The product may subsequently be precipitated with a suitable solvent (ethyl acetate, diethyl ether oder tert.-butylmethyl ether). The resulting precipitate is isolated and dried.

Calculated degree of polymerisation (end group analysis, NMR): x≈4.

IR: ν (in $cm^{-1}$)=3291, 3080, 2925, 1716, 1650, 1537

$^1$H-NMR (DMSO-$d_6$, 400 MHz)=12.378 (s, COOH), 8,145-7,784 (m, CONH), 5.641+5.305 (pseudo-s, $CH_2CCH_3COO$, vinylic protons), 3.378-2.770 (m, backbone), 2.455-2.167 (m, backbone), 1.832 (s, $CH_2CCH_3COO$) ppm.

The product obtained is soluble in wate at a weight ration of product:wate of 1:1.

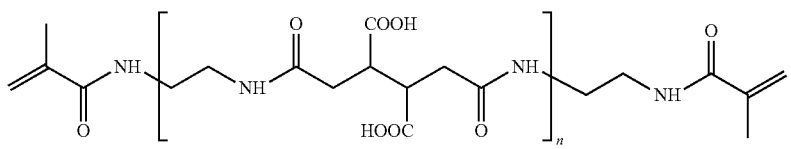

Example 6

Macromonomer 3

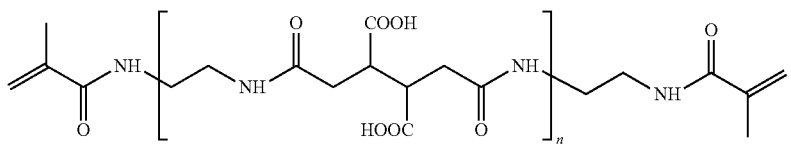

0.044 mol (2.64 g) ethylenediamine (CAS: 107-15-3) are dissolved in 16 mL DMSO. 0.040 mol (7.93 g) butane tetracarboxyalic acid dianhydride are dissolved in 72 mL DMSO and 0.011 mol (1.70 g) methacrylic acid anhydride (CAS: 760-93-0) is added thereto. Both solutions were simultaneously added dropwise to a flask over the same period of time. BHT was added to the mixture as a stabilizer. The reaction mixture is stirred for 16 hours at room temperature. The product may subsequently be precipitated with a suitable solvent (ethyl acetate, diethyl ether oder tert.-butylmethyl ether). The resulting precipitate is isolated and dried.

Calculated degree of polymerisation (end group analysis, NMR): x≈12.

IR: ν (in $cm^{-1}$)=3291, 3079, 2922, 1714, 1645, 1541

$^1$H-NMR (DMSO-$d_6$, 400 MHz)=12.288 (s, COOH), 8.010-7.795 (m, CONH), 5.647+5.311 (pseudo-s, $CH_2CCH_3COO$, vinylic protons), 3.047-2.779 (m, backbone), 2.509-2.083 (m, backbone), 1.843 (s, $CH_2CCH_3COO$) ppm.

The product obtained is soluble in wate at a weight ration of product:wate of 1:1.

Example 7

Formulation Examples

In the following formulation examples, the parts by weight indicated of a surface coated aluminosilicate glass ($d_{50}$=1.7 μm) are mixed with 1.0 parts of a liquid, respectively. The composition of the liquids is described in the following.

In general, samples were stored at 37° C. and at >95% humidity for one hour immediately after preparation, then stored in water at 37° C. for a further 23 hours, before being tested. The biaxial flexural strength values given were measured on discs 20 mm diameter and 1 mm thick, with a supporting knife edge ring support of 15 mm diameter and a pin diameter of 3 mm. The strength values were measured using a Zwick universal testing machine and are reported in MPa. The method is described, for example, in ASTM F 394, and by Wiliams, Billington and Pearson in Dental Materials 2002, Jul., 18 (5), 376-379.

Formulation 1

| | |
|---|---|
| 25.00 Gew.-% | copolymer of acrylic acid and itaconic acid, |
| 25.10 wt.-% | 2-hydroxyethylmethacrylat (HEMA), |
| 4.70 wt.-% | UDMA (urethane dimethacrylate resin, CAS: 105883-40-7), |
| 5.00 wt.-% | tartaric acid, |
| 5.00 wt.-% | macromonomer 1, |
| 34.58 wt.-% | water, |
| 0.29 wt.-% | camphor quinone, |
| 0.33 wt.-% | 4-N,N'-dimethylaminobenzonitrile. |

After homogenization of the above components, the liquid is mixed with 3.0 parts of the glass, test samples are formed and the test samples are illuminated from two sides for curing. After curing, the biaxial flexural strength is determined to be 78.28±5.45 MPa according to the following method.

In general, samples were stored at 37° C. and at >95% humidity for one hour immediately after preparation, then stored in water at 37° C. for a further 23 hours, before being tested. The biaxial flexural strength values given were measured on discs 20 mm diameter and 1 mm thick, with a supporting knife edge ring support of 15 mm diameter and a pin diameter of 3 mm. The strength values were measured using a Zwick universal testing machine and are reported in MPa. The method is described, for example, in ASTM F 394, and by Wiliams, Billington and Pearson in Dental Materials 2002, Jul., 18 (5), 376-379.

Formulation 2

| | |
|---|---|
| 25.00 wt.-% | copolymer of acrylic acid and itaconic acid, |
| 25.10 wt.-% | HEMA, |
| 4.70 wt.-% | UDMA (Urethandimethacrylat-Resin, CAS: 105883-40-7), |
| 5.00 wt.-% | tartaric acid, |
| 9.10 wt.-% | macromonomer 1, |
| 34.64 wt.-% | water, |
| 0.26 wt.-% | camphor quinone, |
| 0.30 wt.-% | 4-N,N'-dimethylamino benzonitrile. |

After homogenization of the above components, the liquid is mixed with 3.0 parts of the glass, test samples are formed and the test samples are illuminated from two sides for curing. After curing, the biaxial strength is determined 67.65±6.80 MPa.

Formulation 3

| | |
|---|---|
| 25.00 wt.-% | copolymer of acrylic acid and itaconic acid, |
| 25.10 wt.-% | HEMA, |
| 9.70 wt.-% | UDMA (Urethandimethacrylat-Resin, CAS: 105883-40-7), |
| 5.00 wt.-% | tartaric acid, |
| 9.10 wt.-% | macromonomer 1, |
| 34.61 wt.-% | water, |
| 0.27 wt.-% | camphor quinone, |
| 0.32 wt.-% | 4-N,N'-dimethylamino benzonitrile. |

After homogenization of the above components, the liquid is mixed with 3.0 parts of the glass, test samples are formed and the test samples are illuminated from two sides for curing. After curing, the biaxial strength is determined 64.55±7.75 MPa.

Formulation 4

| | |
|---|---|
| 25.00 wt.-% | copolymer of acrylic acid and itaconic acid, |
| 25.10 wt.-% | 2-N,N'-bisacrylamido-N,N'-diethyl-1,3-propane, |
| 4.70 wt.-% | UDMA (Urethandimethacrylat-Resin, CAS: 105883-40-7), |
| 5.00 wt.-% | tartaric acid, |
| 5.00 wt.-% | macromonomer 1, |
| 34.58 wt.-% | water, |
| 0.29 wt.-% | camphor quinone, |
| 0.33 wt.-% | 4-N,N'-dimethylaminobenzonitrile. |

After homogenization of the above components, the liquid is mixed with 3.0 parts of the glass, test samples are formed and the test samples are illuminated from two sides for curing. After curing, the biaxial strength is determined: 80.41±7.82 MPa.

Formulation 5

| | |
|---|---|
| 25.00 wt.-% | HEMA modified polyacrylic acid, |
| 25.10 wt.-% | 2-N,N'-bisacrylamido-N,N'-diethyl-1,3-propane, |
| 4.70 wt.-% | UDMA (Urethandimethacrylat-Resin, CAS: 105883-40-7), |
| 5.00 wt.-% | tartaric acid, |
| 5.00 wt.-% | macromonomer 1, |
| 34.58 wt.-% | water, |
| 0.29 wt.-% | camphor quinone, |
| 0.33 wt.-% | 4-N,N'-dimethylamino benzonitrile. |

After homogenization of the above components, the liquid is mixed with 3.0 parts of the glass, test samples are formed and the test samples are illuminated from two sides for curing. After curing, the biaxial strength is determined: 79.68±7.08 MPa.

Formulation 6

| | |
|---|---|
| 25.00 wt.-% | HEMA modified polyacrylic acid, |
| 25.10 wt.-% | 2-N,N'-bisacrylamido-N,N'-diethyl-1,3-propane, |
| 4.70 wt.-% | UDMA (Urethandimethacrylat-Resin, CAS: 105883-40-7), |
| 5.00 wt.-% | tartaric acid, |
| 5.00 wt.-% | macromonomer 3, |
| 34.60 wt.-% | water, |
| 0.28 wt.-% | camphor quinone, |
| 0.32 wt.-% | 4-N,N'-dimethylamino benzonitrile. |

After homogenization of the above components, the liquid is mixed with 3.0 parts of the glass, test samples are formed and the test samples are illuminated from two sides for curing. After curing, the biaxial strength is determined: 70.61±6.65 MPa.

Formulation 7

| | |
|---|---|
| 15.66 wt. % | 2-N,N'-bisacrylamido-N,N'-diethyl-1,3-propane, |
| 31.72 wt. % | macromonomer 3, |
| 45.75 wt. % | water, |
| 5.00 wt. % | tartaric acid, |
| 0.99 wt. % | cumene hydroperoxide, and |
| 0.89 wt. % | benzoylthiourea. |

After mixing of the above components, the liquid is mixed with 3.0 parts of the glass filler, and the adhesion to enamel and dentine was determined to be 4.48±0.89 MPa and 3.82±0.65 MPa, respectively.

The invention claimed is:
1. A dental composition comprising:
(i) a water-soluble polymerizable compound of the following formula (1):

wherein
A is a linear or branched linker group containing at least n nitrogen atoms, wherein the linker group has one or more carboxylic acid groups and is represented by the following formula (3), wherein the nitrogen atom of at least two of the termini forms an amide bond with an X moiety;

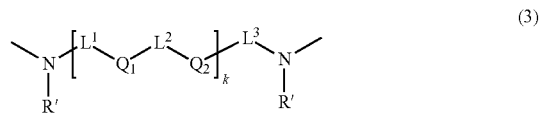

wherein
R' represents a hydrogen atom or a substituted or unsubstituted aliphatic or cycloaliphatic hydrocarbon group, wherein each R' may be the same or different;
$L^1$, $L^2$, and $L^3$ which may be the same or different, independently represent a single bond, or a $C_{2-20}$ straight-chain, branched or cyclic hydrocarbon group optionally containing from 1 to 6 heteroatoms selected from nitrogen and oxygen in the backbone of the hydrocarbon group, and optionally from 1 to 6 functional groups selected from carboxylic acid groups or a salt thereof, hydroxyl groups, thiol groups, and amino groups, and in case a plurality of $L^1$ and $L^2$ are present, each of $L^1$ and $L^2$ may be the same or different;
$Q_1$ and $Q_2$, which may be the same or different, independently represent a single bond or a linkage selected from an amide, a urethane, a urea, and a thiourea linkage;
k is an integer of at least 0,
X are moieties containing a polymerizable double bond and forming an amide bond with a nitrogen atom of A, wherein each X may be the same or different and are represented by the following formula (2):

wherein
$R^1$ and $R^2$ are independent from each other and represent a hydrogen atom, a $C_{1-6}$ alkyl group, or a group $-(CH_2)_m-COOM$, wherein M represents a hydrogen atom or a metal atom and m is an integer of from 0 to 6,
L is a bond or a $C_{1-6}$ alkylene group; and
n is an integer of at least 2; and
(ii) an initiator system.

2. The dental composition according to claim 1, further containing a polyacidic polymer, water, a water soluble solvent, and/or a particulate filler.

3. The dental composition according to claim 1, wherein k is at least 1.

4. The dental composition according to claim 1, wherein the water soluble polymerizable compound of formula (1) has an average molecular weight of from 300 to 10,000.

5. The dental composition according to claim 1 wherein $Q_1$ or $Q_2$ is a single bond and the other of $Q_1$ or $Q_2$ is selected from an amide, a urethane, a urea and a thiourea linkage, and k is at least 1.

6. The dental composition according to claim 2, wherein the water soluble polymerizable compound of formula (1) has an average molecular weight of from 300 to 10,000.

7. The dental composition according to claim 3 wherein the water soluble polymerizable compound of formula (1) has an average molecular weight of from 300 to 10,000.

8. The dental composition according to claim 1, wherein the one or more carboxylic acid groups of the linker group comprises at least two carboxylic acid groups.

9. A dental composition comprising:
(i) a water-soluble polymerizable compound of the following formula (1):

$$AX_n \quad (1)$$

wherein
A is a linear or branched linker group containing at least n nitrogen atoms, wherein the linker group has one or more carboxylic acid groups and is represented by the following formula (3), wherein the nitrogen atom of at least two of the termini forms an amide bond with an X moiety;

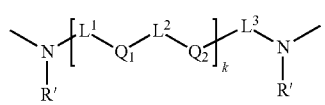

(3)

wherein
R' represents a hydrogen atom or a substituted or unsubstituted aliphatic or cycloaliphatic hydrocarbon group, wherein each R' may be the same or different;

$L^1$, $L^2$, and $L^3$ which may be the same or different, independently represent a single bond, or a $C_{2-20}$ straight-chain, branched or cyclic hydrocarbon group optionally containing from 1 to 6 heteroatoms selected from nitrogen and oxygen in the backbone of the hydrocarbon group, and optionally from 1 to 6 functional groups selected from carboxylic acid groups or a salt thereof, hydroxyl groups, thiol groups, and amino groups, and in case a plurality of $L^1$ and $L^2$ are present, each of $L^1$ and $L^2$ may be the same or different;

$Q_1$ and $Q_2$ represent an amide linkage;

k is an integer of at least 1,

X are moieties containing a polymerizable double bond and forming an amide bond with a nitrogen atom of A, wherein each X may be the same or different and are represented by the following formula (2):

(2)

wherein
$R^1$ and $R^2$ are independent from each other and represent a hydrogen atom, a $C_{1-6}$ alkyl group, or a group $-(CH_2)_m-COOM$, wherein M represents a hydrogen atom or a metal atom and m is an integer of from 0 to 6, L is a bond or a $C_{1-6}$ alkylene group; and n is an integer of at least 2; and (ii) an initiator system.

10. The dental composition according to claim 9, further containing a polyacidic polymer, water, a water soluble solvent, and/or a particulate filler.

11. The dental composition according to claim 10, wherein the water soluble polymerizable compound of formula (1) has an average molecular weight of from 300 to 10,000.

12. The dental composition according to claim 9, wherein the water soluble polymerizable compound of formula (1) has an average molecular weight of from 300 to 10,000.

13. The dental composition according to claim 9, wherein the one or more carboxylic acid groups of the linker group comprises at least two carboxylic acid groups.

* * * * *